United States Patent
Kim et al.

(10) Patent No.: US 6,365,148 B1
(45) Date of Patent: Apr. 2, 2002

(54) ENTERIC COATED MICROGRANULES FOR STABILIZING LACTIC ACID BACTERIA

(75) Inventors: Dong Yeun Kim; Dong Woo Park, both of Seoul; Hong Ryeol Jeon, Suwon-shi, all of (KR)

(73) Assignee: Il Yang Pharm. Co., Ltd., Seoul (KR)

( * ) Notice: Subject to any disclaimer, the term of this patent is extended or adjusted under 35 U.S.C. 154(b) by 0 days.

(21) Appl. No.: 09/529,534

(22) PCT Filed: Oct. 16, 1999

(86) PCT No.: PCT/KR98/00314

§ 371 Date: Apr. 14, 2000

§ 102(e) Date: Apr. 14, 2000

(87) PCT Pub. No.: WO99/20745

PCT Pub. Date: Apr. 29, 1999

(30) Foreign Application Priority Data

Oct. 17, 1997 (KR) .............................. 97-53312

(51) Int. Cl.[7] .......................... A01N 63/00; A61K 9/16; C12N 1/20

(52) U.S. Cl. ................... 424/93.1; 435/252.9; 424/490

(58) Field of Search ............................ 426/42, 61, 317, 426/565; 424/271, 93.45, 93.1, 489, 490; 435/244, 252.1, 252.9

(56) References Cited

U.S. PATENT DOCUMENTS 4,582,799 A * 4/1986 Jarvis, Jr. ...................... 435/4
6,022,568 A * 2/2000 Lesens et al. .................. 426/61

FOREIGN PATENT DOCUMENTS

| CN | 1 124 773 A | | 6/1996 | |
| JP | 62-201823 A2 | | 9/1987 | |
| JP | 62201823 | * | 9/1987 | ................. 435/242 |

* cited by examiner

*Primary Examiner*—Jon P. Weber
*Assistant Examiner*—Patricia A. Patten
(74) *Attorney, Agent, or Firm*—Peter F. Corless; Christine C. O'Day; Edwards & Angell, LLP

(57) ABSTRACT

The present invention relates to an enteric coated granule prepared by coating lactic acid bacteria-containing seed with a water-miscilble coating material and then, if desired, subjecting the first coated product to the second coating with a controlled-release coating material.

15 Claims, No Drawings

ENTERIC COATED MICROGRANULES FOR STABILIZING LACTIC ACID BACTERIA

This application is a 371 of PCT KR98/00314 filed in Korea on Oct. 16, 1998, which claims benefit of priority to KR 1997-53312 filed in Korea on Oct. 17, 1997.

TECHNICAL FIELD

The present invention relates to an enteric coated microgranule for optimally stabilizing lactic acid bacteria. In the present specification, the term "lactic acid bacteria" means the bacteria beneficial to health, which are present in human intestine and help to keep the peristalsis of intestine active.

BACKGROUND ART

The ingested lactic acid bacteria prevent the abnormal fermentation of food and activate the function of intestine, thereby improving the functional abnormality of intestine such as constipation, diarrhea, etc. and maintaining good care of health. Also, the addition of lactic acid bacteria to feedstuff can prevent the accumulation of gas, constipation, diarrhea, etc. caused by the abnormal fermentation inside the intestine of livestock which may result from the repetitive supply of the same feedstuff, which ultimately improves the quality of flesh and highly contributes to the development of dairy farming.

However, in spite of high usefulness and values of lactic acid bacteria, the actual use of lactic acid bacteria has many restrictions due to their acid-unstability. That is, since lactic acid bacteria are very unstable under pH 4, almost all the ingested lactic acid bacteria are destructed at the acidity of gastric juice (about pH 2). Therefore, only a trace amount of the ingested lactic acid bacteria (about one per million) can reach the intestine alive. As a result, much time and expenses are required to make lactic acid bacteria efficiently exhibit their functions in human intestine.

In order to overcome such a problem, a way to increase the amount of lactic acid bacteria which reach the intestine by using more than 10 times excess of bacteria has been proposed in the field of food and pharmaceutical industry. However, it is not a fundamental solution, but merely a very fragmentary and wasting, temporary remedy. Further, food containing microcapsules wherein lactic acid bacteria are mixed with fat, emulsifying agent and protective material and then encapsulated has recently been reported, the purpose of which is to increase the ratio of lactic acid bacteria arrived at the intestine by making the bacteria survive in gastric juice (see, Korean Patent Laid-open Publication No. 97-25405). However, according to the experimental result, it has been identified that upon ingestion of such encapsulated lactic acid bacteria their coating is disintegrated within 30 minutes regardless of the circumstance being gastric juice or intestinal juice. It can also be noted from other experiments that the commercially available lactic acid bacteria coated with gelatin as the coating base are not disintegrated for more than 10 hours in any circumstances without difference on the specificity to gastric juice or intestinal juice (see, Experimental Example 1). It appears that this is because the material used as the coating base for lactic acid bacteria is a conventional one which does not react sensitively to the property of the gastric or intestinal juice. Further, numerous organic solvent-based coating methods utilizing various polymers have been reported in the general pharmaceutical field (see, PCT/JP94/001675, Japanese Patent Appln. Nos. 91-235667, 92-364123, 92-41434, 93-186335, 93-186336, etc.). However, such coating techniques are not satisfactory to protect lactic acid bacteria from gastric juice. Particularly, if organic solvent is used as a solvent of the coated preparation or if the coating process is carried out at a high temperature of more than 55° C., the actual survival rate of lactic acid bacteria in human body is much less than the expected value.

On the other hand, it has been tried to develop variant strains of lactic acid bacteria, which have a high acid-resistance. However, this approach requires greater time and cost, and has worse effect than the coating methods.

DISCLOSURE OF INVENTION

The present inventors have intensively studied about enteric coating technique which gives some usable merits in view of the stability of lactic acid bacteria and in the economical view. As a result, we have found that when lactic acid bacteria are first coated with a specific water-miscible coating material and then, if desired, second coated with a conventional controlled-release coating material, the destruction of lactic acid bacteria during the procedure for preparing the coated granule can be greatly reduced and, furthermore, the coated granule capable of delivering lactic acid bacteria contained therein to the target organ in which lactic acid bacteria actually display their function, i.e. intestine, by safely protecting lactic acid bacteria from the attack of gastric juice can be produced. Thus, we have completed the present invention. In the present invention, since the coated granule contains active lactic acid bacteria in a high ratio and is very sensitive to acidity, the bacteria contained therein can survive under human gastric circumstance and the granule then can be disintegrated rapidly in the intestine.

Therefore, it is an object of the present invention to provide an enteric coated microgranule specially designed so as to display the function of lactic acid bacteria in the intestine by optimally stabilizing lactic acid bacteria contained in the granule.

BEST MODE FOR CARRYING OUT THE INVENTION

The coated granule containing lactic acid bacteria according to the present invention is more specifically explained in below.

The coated granule containing lactic acid bacteria according to the present invention can be prepared by first coating the lactic acid bacteria-containing seed with a water-miscible coating material at low temperature and, if desired, then subjecting the first coated product to the second coating with a controlled-release coating material. In the present invention, the destruction of lactic acid bacteria during the procedure for preparation can be minimized by conducting the first coating with a water-miscible material at low temperature.

In the present invention, one or more strains beneficial to human being, which are selected from the group consisting of Streptococcus genus, Lactococcus genus, Leuconostoc genus, Pediococcus genus, Enterococcus genus, Lactobacillus genus and Bifidobacterium genus can be used as the lactic acid bacteria strain.

The water-miscible coating material which can be used for the first coating includes sodium alginate as the main ingredient of seaweed (e.g., brown seaweed) extract, alginic acid, polymethylmethacrylate [Eudragit L30D, Eudragit LS30D, Kollicoat MAE 3DP (manufactured by BASF Co.), etc.], wheat protein, soybean protein, methylcellulose (MC), hydroxypropylcellulose (HPC), hydroxypropylmethylcellulose [HPMC; pharma coat, aqua coat, etc.], polyvinylacetatephthalate [Sureteric; manufactured by Colorcon Co.], gums, for example, guar gum, locust bean gum, xanthan gum, gellan gum, arabic gum, etc. Since these water-miscible coating materials are water-soluble or water-dispersible, it is advantageous that the first coating procedure can be conveniently carried out by using water as a solvent. This is very important in view of the fact that any organic solvent which is not only harmful to human body but also fatal to the stability of lactic acid bacteria is not used for the coating procedure, and therefore, the problem of removing the residual organic solvent is completely solved. This is a characteristic advantage of the present invention as distinct from the prior techniques which necessarily require the use of organic solvents to dissolve high-molecular substances as a coating material. In the present invention, sodium alginate is preferably used as the water-miscible first coating material. The reason is that since sodium alginate is water-soluble and its aqueous solution is neutral, it is much more advantageous for the stability of lactic acid bacteria.

The seed used for the coating procedure can be either lactic acid bacteria themselves or a mixture of lactic acid bacteria and one or more additive substances selected from the group consisting of starch, lactose, oligosaccharides, glycoalcohols, calcium gluconate, calcium lactate and gluconic acid. These additives are added for the purpose of diluting lactic acid bacteria in a desired ratio, activating only lactic acid bacteria while suppressing other bacteria strains, or improving the proliferation of lactic acid bacteria.

In the first coating procedure, the water-miscible coating material is preferably used in an amount of 1 to 80% by weight with respect to the seed.

Although the first coated granule of lactic acid bacteria as prepared above is sufficiently effective by itself, but it can be more effectively used after second coating with a conventional controlled-release coating material. Therefore, an enteric coated microgranule with both the first and second coatings is also included within the scope of the present invention.

As the second coating material, the controlled-release coating material, particularly an enteric coating material commonly used in pharmaceutical field; or a coating material for swelling such as carbopol or arabic gum; and other controlled-release coating materials can be used. More specifically, corn protein extract (described in USP/NF) and artificial processed materials thereof, such as for example, Zein-DP or prolamin, sodium alginate, alginic acid, polymethylmethacrylate, for example, Eudragit L30D, Eudragit LS30D, Kollicoat MAE 3DP (manufactured by BASF Co.), etc., shellac, hydroxypropylmethylcellulose phthalate (HPMCP), hydroxypropylmethylcellulose (HPMC), hydroxy-propylmethylcelluloseacetatesuccinate (HPMCAS), carboxymethylcellulose (CMC), hydroxypropylcellulose (HPC), celluloseacetatephthalate (CAP), polyvinylacetatephthalate [Sureteric(Colorcon Co.)], ethylcellulose (EC), methylcellulose (MC), soybean protein or wheat protein (they are registered as Food Additives), chitin, chitinic acid, agar, carrageenan, pectin, carbopol, or gums, such as for example, guar gum, locust bean gum, xanthan gum, gellan gum, arabic gum, etc. can be mentioned. Among them, one or more selected from the group consisting of corn protein extract, hydroxypropylmethylcellulose phthalate (HPMCP) and shellac are preferably used as the second coating material.

In conducting the second coating procedure, one or more materials selected from the coating materials as mentioned above are used in an amount of 1 to 95% by weight with respect to the first coated granule. Particularly, when the enteric coating material commonly used in the pharmaceutical field is used, it is used in an amount ranging from 1 to 40% by weight; or when other coating materials for swelling are used, it is used in the amount ranging from 30 to 95% by weight. The kind and amount of the coating material may be appropriately determined by a person skilled in the relevant technical field, considering the property of coating material and the purpose of using the coating material.

Contrary to the first coating wherein only water is used as a solvent for the protection of lactic acid bacteria, the second coating may use one or more various solvents selected from water, alcohol; acetone, acetonitrile, methylene chloride, ether, hexane, chloroform, 1,4-dioxane, tetrahydrofuran, dimethylsulfoxide, ethyl acetate and methyl acetate. In case the coating material is hardly dissolved in the solvent, if required, a pH regulator such as acetic acid, hydrochloric acid, phosphoric acid, various buffer solutions, citric acid, tartaric acid, malic acid, etc. can be used to adjust the pH to the desired range thereby improving the solubility of the coating material. This can be easily carried out by a person skilled in the relevant art.

When both of the first and second coatings are conducted, the coating materials used in the respective steps should be different from each other. If desired, one or more plasticizers selected from a group consisting of polyethyleneglycols, myvacet, propyleneglycol, glycerine, triethyl citrate, triacetin, cetyl alcohol and stearyl alcohol can be used in the first or second coating procedure. In this case, the plasticizer is preferably used in an amount of 1 to 50% by weight with respect to the coating material as used.

To optimally stabilize the lactic acid bacteria in preparing the coated granule, the present invenors have utilized a process in which (a) the seed containing lactic acid bacteria is suspended and, at the same time, spray-coated with a coating-solution, or (b) the seed suspended in the coating-solution is dispersed into a chamber. Thus, the present invention can be carried out more preferably by applying such processes.

The coating process may be carried out by using a fluidized bed granulator, CF-granulator and the like, preferably a fluidized bed granulator (SFC-MINI, Freund co., Japan). When such a granulator is used, the temperature of the introduced air is preferably maintained in the range of 40 to 70° C. The temperature of granule in the granulator at each step should be kept more than 20° C. to prevent the granule from absorbing moisture from the ambient atmosphere and coagulating with each other. Preferably, the temperature of granule is maintained from 25 to 55° C. throughout the whole procedures since lactic acid bacteria may be destroyed at the temperature exceeding 55° C.

The present invention will be more specifically explained by the following examples and experimental examples. However, it should be understood that the examples are intended to illustrate but not to in any manner limit the scope of the present invention.

EXAMPLE 1

(A) First Coating

| Seed: | Lactobacillus acidophilus: | 250 g |
|---|---|---|
| | Lactobacillus bifidus: | |

-continued

| Coating-Solution: | *Streptococcus faecalis* =1:1:1(w/w/w) mixture Sodium alginate Water | 3 g 300 ml |
|---|---|---|

(B) Second Coating

| Seed: | Coated granule according to (A) | 253 g |
|---|---|---|
| Coating-Solution: | Zein-DP(processed from corn protein extract) | 50 g |
| | Cetanol | 5 g |
| | 80% Ethanol | 500 ml |
| | Glycerine | 5 ml | i) Preparation of First Coated Granule

Lactic acid bacteria were suspended in a fluidized bed granulator (SFC-MINI, Freund co., Japan) and, at the same time, spray-coated with the first coating-solution as given above. The operation conditions of the granulator were adjusted to the values given in the following Table 1. Particularly, the temperature of lactic acid bacteria-containing powder, that is the coated powder, in the granulator was carefully controlled not to deviate from the temperature ranging from 25 to 55° C.

ii) Preparation of Second Coated Granule

The first coated granule according to the above procedure i) was suspended in a fluidized bed granulator (SFC-MINI, Freund co., Japan) and, at the same time, spray-coated with the second coating-solution consisting of Zein-DP and 80% ethanol. Glycerine was further added to the coating-solution as a plasticizer. The operating conditions of the granulator were adjusted to the values given in the following Table 1. Particularly, the temperature of lactic acid bacteria-containing powder, that is the coated powder, in the granulator was carefully controlled not to deviate from the temperature ranging from 25 to 55° C.

TABLE 1

| | First Coating | Second Coating |
|---|---|---|
| Temp. of Introduced Air(° C.) | 60 | 60 |
| Temp. of Granule in granulator(° C.) | 30 | 35 |
| Flow rate of Introduced Air(m³/min) | 9 | 9 |
| Flow rate of Excreted Air(m³/min) | 10 | 10 |
| Flow rate of Introduced Air/Slit (m³/min) | 7 | 7 |
| Flow rate of Introduced Air/Fluid (m³/min) | 7 | 7 |
| Spray rate of Coating-Solution (ml/min) | 10 | 12 |
| Flow rate of Sprayed Air(m³/min) | 35 | 35 |
| Rotation Number of Rotor(rpm) | 300 | 300 |
| Rotation Number of Agitator(rpm) | 500 | 500 |
| Rotation Number of Lump Breaker (rpm) | 2500 | 1700 |
| Spur Jet (on-off) | 20 sec. each | 20 sec. each |

EXAMPLE 2

The coated granule according to the present invention was prepared according to the same procedure as Example 1 except that materials as described below were used.

(A) First Coating

| Seed: | *Lactobacillus acidophilus*: *Lactobacillus bifidus*: *Streptococcus faecalis* =1:1:1(w/w/w) mixture | 25 g |
|---|---|---|
| | Lactose | 225 g |
| Coating-Solution: | Sodium Alginate | 3 g |
| | Water | 300 ml |

(B) Second Coating

| Seed: | Coated granule according to (A) | 253 g |
|---|---|---|
| Coating-Solution: | Liquid Shellac (Opaglos ®; Colorcon Co.) | 30 ml |
| | Zein-DP(processed from corn protein extract) | 25 g |
| | Glycerine | 5.0 ml |
| | 80% Ethanol | 300 ml |

EXAMPLE 3

The coated granule according to the present invention was prepared according to the same procedure as Example 1 except that materials as described below were used.

(A) First Coating

| Seed: | *Lactobacillus acidophilus*: *Lactobacillus bifidus*: *Streptococcus faecalis* =1:1:1(w/w/w) mixture | 250 g |
|---|---|---|
| Coating-Solution: | Sodium Alginate | 3 g |
| | Water | 300 ml |

(B) Second Coating

| Seed: | Coated granule according to (A) | 253 g |
|---|---|---|
| Coating-Solution: | HPMCP | 50 g |
| | Ethanol/Acetone Mixture(1/1, v/v) | 700 ml |

EXAMPLE 4

The coated granule according to the present invention was prepared according to the same procedure as Example 1 except that materials as described below were used.

(A) First Coating

| Seed: | *Lactobacillus acidophilus*: *Lactobacillus bifidus*: *Streptococcus faecalis* =1:1:1(w/w/w) mixture | 250 g |
|---|---|---|
| Coating-Solution: | Eudragit L30D | 300 ml |
| | Water | 150 ml |
| | Propylene Glycol | 9 g |

EXAMPLE 5

The coated granule according to the present invention was prepared according to the same procedure as Example 1 except that materials as described below were used.

(A) First Coating

| Seed: | Lactobacillus acidophilus:<br>Lactobacillus bifidus:<br>Streptococcus faecalis<br>=1:1:1(w/w/w) mixture | 125 g |
|---|---|---|
| | Calcium Gluconate | 125 g |
| Coating-Solution: | Sodium Alginate | 3 g |
| | Water | 300 ml |

(B) Second Coating

| Seed: | Coated granule according to (A) | 253 g |
|---|---|---|
| Coating-Solution: | Zein-DP(Processed from Corn protein extract) | 30 g |
| | 80% Ethanol | 500 ml |
| | Glycerine | 5 ml |

EXAMPLE 6

The coated granule according to the present invention was prepared according to the same procedure as Example 1 except that materials as described below were used.

(A) First Coating

| Seed: | Lactobacillus acidophilus:<br>Lactobacillus bifidus:<br>Streptococcus faecalis<br>=1:1:1(w/w/w) mixture | 125 g |
|---|---|---|
| | Xylitol | 125 g |
| Coating-Solution: | Sodium Alginate | 3 g |
| | Water | 300 ml |

(B) Second Coating

| Seed: | Coated granule according to (A) | 253 g |
|---|---|---|
| Coating-Solution: | Chitin | 25 g |
| | Water | 500 ml |
| | Triethyl Citrate | 3 g |
| | Acetic Acid<br>(to control the pH value of solution to 2.5 to 3.0) | q.s. |

EXAMPLE 7

The coated granule according to the present invention was prepared according to the same procedure as Example 1 except that materials as described below were used.

(A) First Coating

| Seed: | Lactobacillus acidophilus:<br>Lactobacillus bifidus:<br>Streptococcus faecalis<br>=1:1:1(w/w/w) mixture | 125 g |
|---|---|---|
| | Galacto-oligosaccharide | 125 g |
| Coating-Solution: | Sodium Alginate | 3 g |
| | Water | 300 ml |

(B) Second Coating

| Seed: | Coated granule according to (A) | 253 g |
|---|---|---|
| Coating-Solution: | Carbopol 940(Carbomer ® 940) | 10 g |
| | Water | 500 ml |

EXAMPLE 8

The coated granule according to the present invention was prepared according to the same procedure as Example 1 except that materials as described below were used.

(A) First Coating

| Seed: | Lactobacillus acidophilus:<br>Lactobacillus bifidus:<br>Streptococcus faecalis<br>=1:1:1(w/w/w) mixture | 125 g |
|---|---|---|
| | Calcium Gluconate | 125 g |
| Coating-Solution: | Sodium Alginate | 3 g |
| | Water | 300 ml |

(B) Second Coating

| Seed: | Coated granule according to (A) | 253 g |
|---|---|---|
| Coating-Solution: | Soybean Protein | 30 g |
| | Water<br>(phosphate buffer, pH 7.2) | 500 ml |
| | Glycerine | 5 ml |

EXAMPLE 9

The coated granule according to the present invention was prepared according to the same procedure as Example 1 except that materials as described below were used.

(A) First Coating

| Seed: | Lactobacillus acidophilus:<br>Lactobacillus bifidus:<br>Streptococcus faecalis<br>=1:1:1(w/w/w) mixture | 125 g |
|---|---|---|
| | Mannitol | 125 g |
| Coating-Solution: | Sodium Alginate | 3 g |
| | Water | 300 ml |

(B) Second Coating

| Seed: | Coated granule according to (A) | 253 g |
|---|---|---|
| Coating-Solution: | Xanthan Gum | 20 g |
| | Water | 500 ml |
| | Glycerine | 5 ml |

Experimental Example 1

In order to examine whether the coated granules prepared in Examples 1 to 9 exhibit any changes in artificial gastric juice and intestinal juice [which are prepared according to USP], the following in vitro experiments were conducted. Then, the results thus obtained were compared with those of commercially available products, Dr. Capsule (Binggrae Co.) and Bifidus strain original powder-1 ($10^8$ times) (Cell Biotech. Co.).

First, 10 g of each of coated lactic acid bacteria was stirred in $100_{ml}$ of artificial gastric juice for one hour at 50 rpm and then the residue was transferred to $100_{ml}$ of artificial intestinal juice. The coated lactic acid bacteria were slowly stirred for 5 hours in artificial intestinal juice and then incubated (cuture medium: Elliker broth; curture condition: anaerobic, 37° C., 72 hours). Then, the disintegration degree of lactic acid bacteria was determined by checking the time when a spongy phase was macroscopically observed. In Table 2, the disintegration data in artificial intestinal juice means the time when 100% of the coated granule is disintegrated and the survival rate was calculated according to the following equation:

$$\text{Survival rate} = \frac{A}{B} \times 100$$

In the above equation,
   A represents the number of lactic acid bacteria obtained by stirring for one hour in gastric juice and for 5 hours in intestinal juice and then incubating, and
   B represents the number of lactic acid bacteria obtained by stirring for 5 hours only in intestinal juice and then incubating.
   Each of the results represented in Table 2 is an average value of three runs.
Table 2
Acid-resistance(Survival Rate) and Disintegration Data of Coated Lactic Acid Bacteria

|  | Disintegration | | | |
| --- | --- | --- | --- | --- |
|  | In artificial gastric juice (one hour; pH 1.2) | In artificial intestinal juice (5 hours; pH 6.8) | Survival Rate(%) | Remarks |
| Example 1 | No change | Within 3 hours | 65 | |
| Example 2 | No change | Within 2 hours | 43 | |
| Example 3 | No change | Within 2 hours | 55 | |
| Example 4 | No change | Within 1 hour | 35 | |
| Example 5 | No change | Within 3 hours | 23 | |
| Example 6 | No change | Within 2 hours | 31 | |
| Example 7 | No change | Within 1 hour | 27 | |
| Example 8 | No change | Within 2 hours | 25 | |
| Example 9 | No change | Within 2 hours | | |
| Product A | No change | More than 5 hours | 17 | Gelatin coating |
| Product B | No change | Within 1 hour | 3 | |

Note) Product A: Dr. Capsule (Binggre Co., Korea)
Product B: Pasteur VIP (Pasteur Co., Korea)

As can be seen from the results given in the above Table 2, the coated granule of lactic acid bacteria of the present invention exhibits a superior survival rate in artificial gastric juice and further, can be disintegrated rapidly in the intestine, in comparison with the commercially available prior products. Therefore, the coated granule of lactic acid bacteria as prepared according to the present invention is recognized as the optimal form which can regulate the in vivo activity of lactic acid bacteria in the best manner.

What is claimed is:
1. An enteric coated granule consisting of a seed obtained from spray-coating lactic acid bacteria powder with a water-miscible coating material while suspending the powder in a chamber, wherein the water-miscible coating material is one or more selected from the group consisting of sodium alginate, polymethylmethacrylate, wheat protein, soybean protein, methylcellulose, hydroxypropylcellulose, hydroxypropylmethylcellulose, polyvinylacetate phthalate, guar gum, locust bean gum, xanthan gum, gellan gum and arabic gum.

2. The coated granule according to claim 1, wherein lactic acid bacteria is one or more selected from the group consisting of the strains belonging to Streptococcus genus, Lactococcus genus, Leuconostoc genus, Pediococcus genus, Enterococcus genus, Lactobacillus genus and Bifidobacterium genus.

3. The coated granule according to claim 1, wherein the water-miscible coating material is sodium alginate.

4. The coated granule according to claim 1 or 3, wherein the water-miscible coating material is used in an amount of 1 to 80% by weight with respect to the powder.

5. The coated granule according to claim 1, wherein after coating with a water-miscible coating material, the seed is further coated with a controlled-release coating material.

6. The coated granule according to claim 5, wherein the controlled-release coating material is one or more selected from the group consisting of corn protein extract and processed materials thereof, sodium alginate, alginic acid, polymethylmethacrylate, shellac, hydroxypropylmethylcellulosephthalate, hydroxypropylmethylcellulose, hydroxypropylmethylcellulose acetate succinate, carboxymethylcellulose, hydroxypropylcellulose, celluloseacetatephthalate, polyvinylacetatephthalate, ethylcellulose, methylcellulose, soybean protein, wheat protein, chitin, chitinic acid, agar, carrageenan, pectin, carbopol, guar gum, locust bean gum, xanthan gum, gellan gum and arabic gum.

7. The coated granule according to claim 6, wherein the controlled-release coating material is one or more selected from the group consisting of corn protein extract, hydroxypropylmethylcellulosephthalate and shellac.

8. The coated granule according to claim 6 or 7, wherein the controlled-release coating material is used in an amount of 1 to 95% by weight with respect to the seed.

9. The coated granule according to claim 5, wherein one or more solvents selected from the group consisting of water, alcohol, acetone, acetonitrile, methylene chloride, ether, hexane, chloroform, 1,4-dioxane, tetrahydrofuran, dimethylsulfoxide, ethyl acetate and methyl acetate are used for coating with a controlled-release coating material.

10. The coated granule according to claim 1 or 5, wherein one or more plasticizers selected from the group consisting of polyethyleneglycols, myvacet, propyleneglycol, glycerine, triethyl citrate, triacetin, cetyl alcohol and stearyl alcohol are mixed with the coating material.

11. The coated granule according to claim 10, wherein the plasticizer is used in an amount of 1 to 50% by weight with respect to the coating material.

12. The coated granule according to claim 1 or 5, wherein the coating procedure is carried out at the temperature ranging from 20 to 55° C.

13. The coated granule of claim 1, wherein the seed further comprises a carrier.

14. The coated granule of claim 13 wherein the carrier is one or more substances selected from the group consisting of starch, lactose, oligosaccharides, glycoalcohols, calcium gluconate, calcium lactate and gluconic acid.

15. The coated granule of claim 1 wherein the water-miscible coating is applied with a solvent of water and substantially in the absence of an organic solvent.

* * * * *